United States Patent [19]
Beard

[11] 3,976,654
[45] Aug. 24, 1976

[54] 2-SUBSTITUTED-1,2,4-THIADIAZOLO-[2,3-a]-BENZIMIDAZOLES AND PROCESS FOR THEIR PREPARATION

[75] Inventor: Colin C. Beard, Palo Alto, Calif.

[73] Assignee: Syntex (U.S.A.) Inc., Palo Alto, Calif.

[22] Filed: Oct. 16, 1975

[21] Appl. No.: 622,932

Related U.S. Application Data

[62] Division of Ser. No. 523,765, Nov. 14, 1974, Pat. No. 3,846,031, which is a division of Ser. No. 403,474, Oct. 4, 1973, Pat. No. 3,880,874.

[52] U.S. Cl. .................... 260/294.8 B; 260/250 BN; 260/256.5 R; 260/306.8 F; 260/309.2; 424/250; 424/251; 424/263; 424/270
[51] Int. Cl.² .................................. C07D 213/34
[58] Field of Search ...................... 260/294.8 B

[56] References Cited
UNITED STATES PATENTS 3,225,059  12/1965  D'Amico .................. 260/306.8 F
3,726,891   4/1973  Pilgram et al. ........... 260/306.8 F Primary Examiner—Alan L. Rotman
Attorney, Agent, or Firm—Gerard A. Blaufarb; William B. Walker

[57] ABSTRACT

Novel 2-substituted-1,2,4-thiadiazolo-[2,3-a]-benzimidazoles of the formula

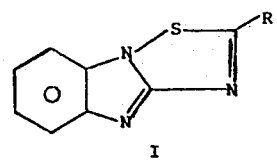

I and the pharmaceutically acceptable salts thereof; and process for their preparation. These 2-substituted-1,2,4-thiadiazolo-[2,3-a]-benzimidazoles are useful as fungistatic and fungicidal agents.

5 Claims, No Drawings

2-SUBSTITUTED-1,2,4-THIADIAZOLO-[2,3-a]-BENZIMIDAZOLES AND PROCESS FOR THEIR PREPARATION

This is a division of application Ser. No. 523,765, filed Nov. 14, 1974, now U.S. Pat. No. 3,846,031, which is in turn a division of application Ser. No. 403,474, filed Oct. 4, 1973, now U.S. Pat. No. 3,880,874, issued Apr. 29, 1975.

This invention relates to novel 2-substituted-1,2,4-thiadiazolo-[2,3-a]-benzimidazole compounds of the formula:

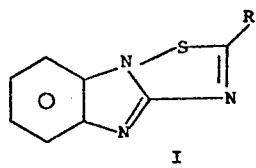

wherein R is the pharmaceutically acceptable salts thereof, and processes for the preparation thereof.

The terms lower alkoxy, lower alkyl, lower alkylthio, and lower alkylsulfinyl as used above and in the claims are inclusive of moieties containing from 1 to 4 carbon atoms, for example, methyl, ethyl, propyl, isopropyl, butyl and tert.-butyl.

The term "halo" as used above and in the claims is inclusive of chloro, bromo, fluoro and iodo.

The compounds of Formula I are chemotherapeutic agents which possess fungistatic and fungicidal properties and thus are useful in combatting fungus infections.

Amongst the fungi against which the compounds of Formula I exhibit fungistatic and fungicidal activity are:

| | |
|---|---|
| M. andounini | H. gramineum |
| E. floccusum | M. gypsum |
| T. mentagrophytes | M. canis |
| C. albicans | T. rubrum |
| Cr. neoformans | T. tonsurans |
| R. solani | T. schoenleinii |
| A. solani | |

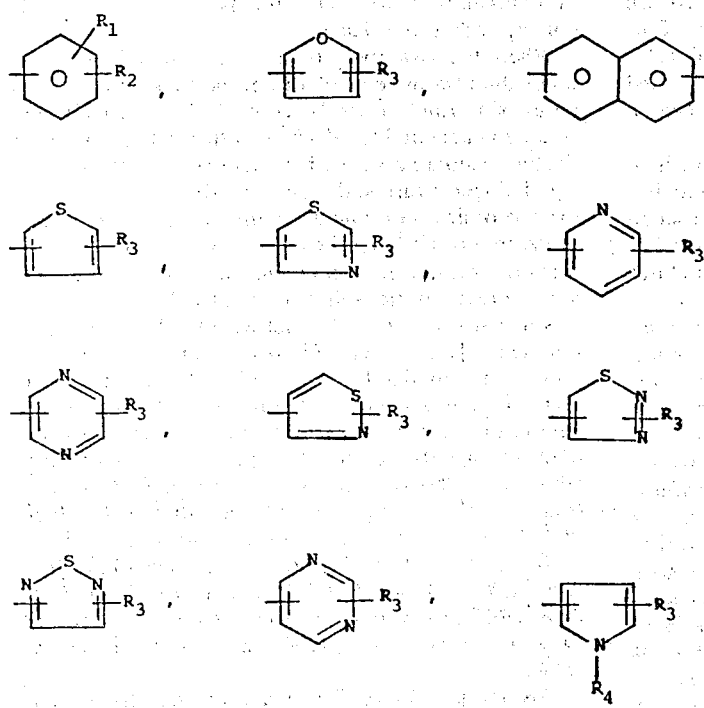

wherein $R_1$ and $R_2$ are each hydrogen, lower alkoxy, halo, nitro, lower alkyl, lower alkylthio, lower alkylsulfinyl, or trifluoromethyl;

$R_3$ is hydrogen, lower alkoxy, halo, nitro, or lower alkyl; and $R_4$ is hydrogen or lower alkyl; and Particularly preferred are those compounds of Formula I wherein R is phenyl, 4-chlorophenyl, 4-methoxyphenyl, 4-methylphenyl, 4-methylthiophenyl, 4-methylsulfinylphenyl, 4-tert.-butylphenyl, 4-trifluoromethylphenyl, 2-furyl, 3-furyl, 2-naphthyl 2-thienyl, 3-thienyl, 2-thiazolyl, 4-thiazolyl, 5-thiazolyl, 2- methyl-4-thiazolyl, 2-pyridyl, 3-pyridyl, 4-pyridyl, 2-pyrazinyl, 3-isothiazolyl, 4-isothiazolyl, 5-isothiazolyl, 1,2,3-thiadiazolyl, and 1,2,5-thiadiazolyl.

The compounds of Formula I are prepared according to the following generalized reaction scheme:

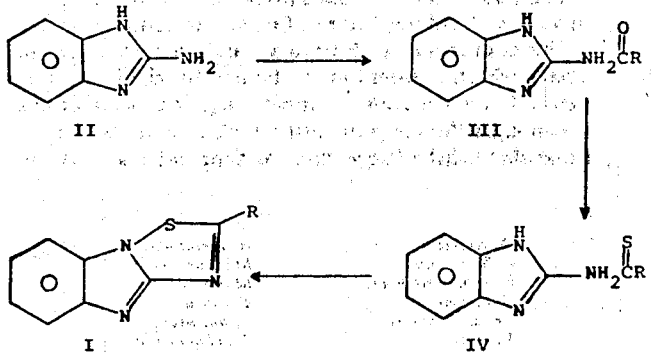

wherein R is defined as above.

The carbonylamino compounds of Formula III are obtained by treating the 2-aminobenzimidazole of Formula II with an acid chloride (RCOCl), acid ester (RCOOR$_5$, wherein R$_5$ is methyl or ethyl), or the mixed anhydride of a free acid (RCOOH) and trifluoroacetic acid.

The reaction of the compounds of Formula II with an acid chloride (RCOCl) to obtain the carbonylamino compounds of Formula III is carried out in the presence of an organic solvent, e.g., pyridine, acetone, tetrahydrofuran, and the like, at a temperature of from about −40° to 35°C. for from about 2 to 20 hours.

The reaction of the compound of Formula II with an acid ester (RCOOR$_5$) to obtain the carbonylamino compounds of Formula III is carried out at a temperature of from about 100° to 200°C. for from about 1 to 20 hours.

The reaction of the compound of Formula II with a mixed anhydride of a free acid (RCOOH) and trifluoroacetic acid, prepared from the free acid and trifluoroacetic acid anhydride, to obtain the carbonylamino compounds of Formula III is carried out in the presence of an inert organic solvent, e.g., tetrahydrofuran, acetone, and the like, and in the presence of a base, e.g., triethylamine, and the like, at a temperature of from about −20° to 30°C. for from about 1 to 20 hours.

The thus-obtained carbonylamino compounds of Formula III, obtained by reaction with an acid chloride, acid ester, or mixed anhydride, as described above, are then converted to the corresponding thionylcarbonylamino compounds of Formula IV by treatment with phosphorous pentasulfide (P$_2$S$_5$), in an inert organic solvent, e.g., pyridine, dioxane, and the like, at a temperature of from about 80° to 120°C., for from about 1 to 20 hours.

The 2-substituted 1,2,4-thiadiazolo-[2,3-a]-benzimidazole compounds of Formula I are obtained by treating the compounds of Formula IV with an oxidizing agent, e.g., m-chloroperbenzoic acid, bromine, chlorine, sulfuryl chloride, peracetic acid, hydrogen peroxide, and the like, at a temperature of from about −40° to 40°C., for from about ¼ to 6 hours, in an inert organic solvent, e.g., chloroform, and the like. When the reaction is carried out using bromine or chlorine it is preferred that the temperature be between about 0° and 30°C. In addition, when the oxidation reaction is carried out using bromine or chlorine, the compounds of Formula I can, if desired, be isolated as their pharmaceutically acceptable hydrobromide or hydrochloride salts, or treated with a base, e.g., ammonia, sodium or potassium bicarbonate and the like, to obtain the corresponding free bases.

When the oxidation reaction is carried out using other than bromine or chlorine, the thus-obtained free bases of Formula I can be converted to their pharmaceutically acceptable salts by reaction with pharmaceutically acceptable acids, for example, inorganic acids, e.g., halogen hydroacids (particularly hydrochloric and hydrobromic), nitric acid, phosphoric acids, sulphonic acids, mono- and dicarboxylic acids, and the like; and organic acids, e.g., acetic, maleic, succinic, tartaric, lactic, citric, sorbic, salicylic, and the like.

Alternatively, the 2-(methylsulfinylphenyl)-1,2,4-thiadiazolo[2,3-a]-benzimidazole compounds of Formula I are obtained by subjecting the corresponding 2-(methylthiophenyl)-1,2,4-thiadiazolo-[2,3-a]-benzimidazole compounds to a further oxidation with an oxidizing agent, e.g., m-chloroperbenzoic acids, peracetic acid, and the like, in the presence of an inert organic solvent, e.g., chloroform, dichloromethane, and the like, at temperatures of from about −30° to 30°C. for from ½ to 24 hours. The thus-obtained 2-(methylsulfinylphenyl)-1,2,4-thiadiazolo-[2,3-a]-benzimidazole compounds can then be converted to their pharmaceutically acceptable salts as previously described.

The compounds of Formula I, or the pharmaceutically acceptable salts thereof, can be formulated into solutions, creams and ointments, according to methods known to those skilled in the art, for topical administration. Preferably a concentration of from about 0.5 to 5 percent of the active ingredient is used.

It is to be understood that isolation of the compounds described herein can be effected by any suitable separation or purification procedure, such as, for example, extraction, filtration, evaporation, distillation, crystallization, thin-layer chromatography or column chromatography, or a combination of these procedures. Illustrations of suitable separation and isolation procedures can be had by reference to the examples described herein below. However, other equivalent separation or isolation procedures could, of course, also be used.

A further understanding of the invention can be had from the following non-limiting examples. Also, where necessary, examples are repeated to provide starting materials for subsequent examples.

EXAMPLE 1

A. A solution of 20 g. of 2-aminobenzimidazole (II) in 150 ml. of pyridine is cooled to −20°C. and 20 g. of 3-furoyl chloride is added thereto. The thus-obtained reaction mixture is allowed to warm slowly to between 20°–30°C. (room temperature), and maintained at this temperature for 15 hours, diluted with water and filtered to give a residue which is recrystallized from acetic acid to yield 2-(3-furylcarbonylamino)-benzimidazole [(III), R = 3-furyl].

Similarly, substituting a stoichiometric equivalent amount of benzoyl chloride,
4-chlorobenzoyl chloride,
4-methoxybenzoyl chloride,
4-methylbenzoyl chloride,
4-methylthiobenzoyl chloride,
4-methylsulfinylbenzoyl chloride,
4-tert.-butylbenzoyl chloride,
4-trifluoromethylbenzoyl chloride,
2-furoyl chloride,
2-naphthoyl chloride,
2-thenoyl chloride,
3-thenoyl chloride,
4-thiazoloyl chloride,
5-thiazoloyl chloride,
2-methyl-4-thiazoloyl chloride,
1,2,3-thiadiazol-4-oyl chloride, and
1,2,5-thiadiazol-3-oyl chloride, for 3-furoyl chloride in the procedure of Example 1A is productive of
2-phenylcarbonylamino-benzimidazole
2-(4-chlorophenylcarbonylamino)-benzimidazole,
2-(4-methoxyphenylcarbonylamino)-benzimidazole,
2-(4-methylphenylcarbonylamino)-benzimidazole,
2-(4-methylthiophenylcarbonylamino)-benzimidazole,
2-(4-methylsulfinylphenylcarbonylamino)-benzimidazole,
2-(4-tert.-butylphenylcarbonylamino)-benzimidazole,
2-(4-trifluoromethylphenylcarbonylamino)-benzimidazole,
2-(2-furylcarbonylamino)-benzimidazole,
2-(2-naphthylcarbonylamino)-benzimidazole,
2-(2-thienylcarbonylamino)-benzimidazole,
2-(3-thienylcarbonylamino)-benzimidazole,
2-(4-thiazolylcarbonylamino)-benzimidazole,
2-(5-thiazolylcarbonylamino)-benzimidazole,
2-(2-methyl-4-thiazolylcarbonylamino-benzimidazole,
2-(1,2,3-thiadiazol-4-ylcarbonylamino)-benzimidazole, and
2-(1,2,5-thiadiazol-3-ylcarbonylamino)-benzimidazole, respectively.

B. A mixture of 9 g. of 2-aminobenzimidazole (II) and 10 g. of 3-pyridinecarboxylic acid methyl ester (methyl nicotinate) is heated at 150°–160°C. for about 10 hours. The reaction mixture is then triturated with 50 ml. of hot methanol, followed by filtration to yield a residue comprising 2-(3-pyridylcarbonylamino)-benzimidazole [(III), R = 3-pyridyl].

Similarly, substituting a stoichiometric equivalent amount of 2-thiazolecarboxylic acid methyl ester,
2-pyridinecarboxylic acid methyl ester, and
4-pyridinecarboxylic acid methyl ester
for 3-pyridinecarboxylic acid methyl ester in the procedure of Example 1B is productive of 2-(2-thiazolylcarbonylamino)-benzimidazole,
2-(2-pyridylcarbonylamino)-benzimidazole, and
2-(4-pyridylcarbonylamino)-benzimidazole, respectively.

C. 3.7 G. of 2-pyrazinecarboxylic acid is suspended in 20 ml. of dry tetrahydrofuran and 6.3 g. of trifluoroacetic anhydride is added thereto. To the resulting solution, at 20°–25°C., there is added 8.5 ml. of triethylamine and 4 g. of 2-aminobenzimidazole (II) and the thus-obtained reaction mixture is stirred at 20°–25°C. for about 5 hours. 200 Ml. of water is then added, followed by filtration and the residue is recrystallized from aqueous acetic acid to yield 2-(2-pyrazinylcarbonylamino)-benzimidazole [(III), R = 2-pyrazinyl].

Similarly, substituting a stoichiometric equivalent amount of
3-isothiazolecarboxylic acid,
4-isothiazolecarboxylic acid, and
5-isothiazolecarboxylic acid, for 2-pyrazinecarboxylic acid in the procedure of Example 1C is productive of 2-(3-isothiazolylcarbonylamino)-benzimidazole,
2-(4-isothiazolylcarbonylamino)-benzimidazole, and
2-(5-isothiazolylcarbonylamino)-benzimidazole, respectively.

EXAMPLE 2

To 10 g. of 2-(3-furylcarbonylamino)-benzimidazole [(III), R = 3-furyl] in 200 ml. of pyridine is added 10 g. of phosphorous pentasulfide and the reaction mixture is heated to 100°–110°C. for ten hours. The bulk of the pyridine is removed under vacuum and the residue is treated with 500 ml. of saturated potassium bicarbonate solution, filtered and recrystallized from methanol-chloroform to yield 2-(3-furylthiocarbonylamino)-benzimidazole [(IV), R = 3-furyl].

Similarly, substituting a stoichiometric equivalent amount of the other compounds obtained in Example 1A; the compounds obtained in Example 1B; and the compounds obtained in Example 1C; for 2-(3-furylcarbonylamino)-benzimidazole, and following the procedure of Example 2 is productive of 2-phenylthiocarbonylamino-benzimidazole,
2-(4-chlorophenylthiocarbonylamino)-benzimidazole,
2-(4-methoxyphenylthiocarbonylamino)-benzimidazole,
2-(4-methylphenylthiocarbonylamino)-benzimidazole,
2-(4-methylthiophenylthiocarbonylamino)-benzimidazole,
2-(4-methylsulfinylphenylthiocarbonylamino)-benzimidazole,
2-(4-tert.-butylphenylthiocarbonylamino)-benzimidazole,
2-(4-trifluoromethylphenylthiocarbonylamino)-benzimidazole,
2-(2-furylthiocarbonylamino)-benzimidazole,
2-(2-naphthylthiocarbonylamino)-benzimidazole, 2-(2-thienylthiocarbonylamino)-benzimidazole,
2-(3-thienylthiocarbonylamino)-benzimidazole,
2-(4-thiazolylthiocarbonylamino-benzimidazole,
2-(5-thiazolylthiocarbonylamino)-benzimidazole,
2-(2-methyl-4-thiazolylthiocarbonylamino)-benzimidazole,
2-(1,2,3-thiadiazol-4-ylthiocarbonylamino)-benzimidazole, and
2-(1,2,5-thiadiazol-3-ylthiocarbonylamino)-benzimidazole;
2-(3-pyridylthiocarbonylamino)-benzimidazole,
2-(2-thiazolylthiocarbonylamino)-benzimidazole,
2-(2-pyridylthiocarbonylamino)-benzimidazole, and
2-(4-pyridylthiocarbonylamino)-benzimidazole;
2-(2-pyrazinylthiocarbonylamino)-benzimidazole,
2-(3-isothiazolylthiocarbonylamino)-benzimidazole,
2-(4-isothiazolylthiocarbonylamino)-benzimidazole, and
2-(5-isothiazolylthiocarbonylamino)-benzimidazole, respectively.

EXAMPLE 3

A. To 4.8 g. of 2-(3-furylthiocarbonylamino)-benzimidazole [(IV), R = 3-furyl] in 200 ml. of chloroform at 20°–30°C. (room temperature) is added 1.1 ml. of bromine. After 1 hour, the reaction mixture is filtered and the residue (the hydrobromide salt) is treated with 500 ml. of chloroform and 50 ml. of aqueous ammonia. The chloroform layer is separated, dried over magnesium sulfate, and concentrated. The product is recrystallized from methanol-chloroform to yield 2-(3-furyl)-1,2,4-thiadiazolo-[2,3-a]-benzimidazole [(I), R = 3-furyl].

Similarly, substituting a stoichiometric equivalent amount of other compounds obtained in Example 2, 2-phenylthiocarbonylamino-benzimidazole,
2-(4-chlorophenylthiocarbonylamino)-benzimidazole,
2-(4-methoxyphenylthiocarbonylamino-benzimidazole,
2-(4-methylphenylthiocarbonylamino)-benzimidazole,
2-(4-methylthiophenylthiocarbonylamino)-benzimidazole,
2-(4-methylsulfinylthiocarbonylamino)-benzimidazole,
2-(4-tert.-butylphenylthiocarbonylamino)-benzimidazole,
2-(4-trifluoromethylphenylthiocarbonylamino)-benzimidazole,
2-(2-furylthiocarbonylamino)-benzimidazole,
2-(2-naphthylthiocarbonylamino)-benzimidazole,
2-(2-thienylthiocarbonylamino)-benzimidazole,
2-(3-thienylthiocarbonylamino)-benzimidazole,
2-(2-thiazolylthiocarbonylamino)-benzimidazole,
2-(4-thiazolylthiocarbonylamino)-benzimidazole,
2-(5-thiazolylthiocarbonylamino)-benzimidazole,
2-(2-methyl-4-thiazolylthiocarbonylamino)-benzimadazole,
2-(3-pyridylthiocarbonylamino)-benzimidazole,
2-(4-pyridylthiocarbonylamino)-benzimidazole,
2-(3-isothiazolylthiocarbonylamino)-benzimidazole,
2-(4-isothiazolylthiocarbonylamino)-benzimidazole,
2-(5-isothiazolylthiocarbonylamino)-benzimidazole,
2-(1,2,3-thiadiazol-4-ylthiocarbonylamino)-benzimidazole, and
2-(1,2,5-thiadiazol-3-ylthiocarbonylamino)-benzimidazole, for 2-(3-furylthiocarbonylamino)-benzimidazole in the procedure of Example 3A is productive of 2-phenyl-1,2,4-thiadiazolo-[2,3-a]-benzimidazole,
2-(4-chlorophenyl)-1,2,4-thiadiazolo-[2,3-a]-benzimidazole,
2-(4-methoxyphenyl)-1,2,4-thiadiazolo-[2,3-a]-benzimidazole,
2-(4-methylphenyl)-1,2,4-thiadiazolo-[2,3-a]-benzimidazole,
2-(4-methylthiophenyl)-1,2,4-thiadiazolo-[2,3-a]-benzimidazole,
2-(4-methylsulfinylphenyl)-1,2,4-thiadiazolo-[2,3-a]-benzimidazole,
2-(4-tert.-butylphenyl)-1,2,4-thiadiazolo-[2,3-a]-benzimidazole,
2-(4-trifluoromethylphenyl)-1,2,4-thiadiazolo-[2,3-a]-benzimidazole,
2-(2-furyl)-1,2,4-thiadiazolo-[2,3-a]-benzimidazole,
2-(2-naphthyl)-1,2,4-thiadiazolo-[2,3-a]-benzimidazole,
2-(2-thienyl)-1,2,4-thiadiazolo-[2,3-a]-benzimidazole,
2-(3-thienyl)-1,2,4-thiadiazolo-[2,3-a]-benzimidazole,
2-(2-thiazolyl)-1,2,4-thiadiazolo-[2,3-a]-benzimidazole,
2-(4-thiazolyl)-1,2,4-thiadiazolo-[2,3-a]-benzimidazole,
2-(5-thiazolyl)-1,2,4-thiadiazolo-[2,3-a]-benzimidazole,
2-(2-methyl-4-thiazolyl)-1,2,4-thiadiazolo-[2,3-a]-benzimidazole,
2-(3-pyridyl)-1,2,4-thiadiazolo-[2,3-a]-benzimidazole,
2-(4-pyridyl)-1,2,4-thiadiazolo-[2,3-a]-benzimidazole,
2-(3-isothiazolyl)-1,2,4-thiadiazolo-[2,3-a]-benzimidazole,
2-(4-isothiazolyl)-1,2,4-thiadiazolo-[2,3-a]-benzimidazole,
2-(5-isothiazolyl)-1,2,4-thiadiazolo-[2,3-a]-benzimidazole,
2-(1,2,3-thiadiazol-4-yl)-1,2,4-thiadiazolo-[2,3-a]-benzimidazole, and
2-(1,2,5-thiadiazol-3-yl)-1,2,4-thiadiazolo-[2,3-a]-benzimidazole, respectively.

B. To 0.51 g. of 2-(2-pyrazinylthiocarbonylamino)-benzimidazole [(IV), R = 2-pyrazinyl] in 200 ml. of chloroform at 20°–30°C. (room temperature) is added 0.5 g. of m-chloroperbenzoic acid. The reaction mixture is allowed to stand for 15 hours (overnight) and washed with 20 ml. of potassium bicarbonate solution, 20 ml. of water and dried over magnesium sulfate. The chloroform is evaporated and the residue is recrystallized from methanol-chloroform to yield 2-(2-pyrazinyl)-1,2,4-thiadiazolo-[2,3-a]-benzimidazole [(I), R = 2-pyrazinyl].

Similarly, substituting a stoichiometric equivalent amount of 2-(2-pyridylthiocarbonylamino)-benzimidazole for 2-(2-pyrazinylthiocarbonylamino)-benzimidazole in the procedure of Example 3B is productive of 2-(2-pyridyl)-1,2,4-thiadiazolo-[2,3-a]-benzimidazole.

C. To 0.28 g. 2-(4-methylthiophenyl)-1,2,4-thiadiazolo-benzimidazole [(I), R = 4-methylthiophenyl] in 250 ml. of chloroform and 5 ml. of methanol at 20°C. is added 0.2 g. of m-chloroperbenzoic acid in 20 ml. of chloroform. The reaction mixture is allowed to stand at 20°–25°C. for 5 hours, washed with 20 ml. of dilute sodium bicarbonate solution, 20 ml. of water and dried over magnesium sulfate. The chloroform solution is concentrated and the residue remaining is recrystallized from methanol-chloroform to yield 2-(4-methylsulfinylphenyl)-1,2,4-thiadiazolo-[2,3-a]-benzimidazole.

In the Examples above, specific reaction sequences have been extended, in a general sense, to the preparation of other similar and related compounds It should be understood, however, that with respect to any compound which has been prepared by the extension of a specific reaction sequence, it may be necessary or desirable to utilize solvents, reaction media, recrystallization media, reaction times or temperatures, etc., other than the ones given in the specific reaction sequence upon which such extension is based. Additionally, the specific reaction sequence or manner in which particular compounds are to be prepared will depend, inter alia, upon the availability of the necessary starting materials, or the ease in which the desired starting materials can be prepared, and the reactivity thereof. These variations are deemed to be within the skill of those working in this art and will be apparent from a consideration of the particular reactants utilized and/or particular compound desired to be produced.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A compound represented by the formula:

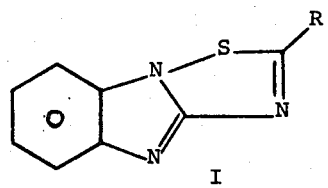

wherein R is

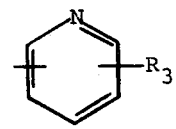

in which $R_3$ is hydrogen, lower alkoxy, halo, nitro, or lower alkyl; and the pharmaceutically acceptable salts thereof.

2. A compound of claim 1 wherein R is 2-pyridyl, 3-pyridyl or 4-pyridyl.

3. The compound of claim 2 wherein R is 2-pyridyl, 2-(2-pyridyl)-1,2,4-thiadiazolo-[2,3-a]-benzimidazole.

4. The compound of claim 2 wherein R is 3-pyridyl, 2-(3-pyridyl)-1,2,4-thiadiazolo-[2,3-a]-benzimidazole.

5. The compound of claim 2 wherein R is 4-pyridyl, 2-(4-pyridyl)-1,2,4-thiadiazolo-[2,3-a]-benzimidazole.

* * * * *